United States Patent [19]
McCabe et al.

[11] Patent Number: 5,868,676
[45] Date of Patent: Feb. 9, 1999

[54] INTERACTIVE DOPPLER PROCESSOR AND METHOD

[75] Inventors: Laurence S. McCabe, Sunnyvale; Donald R. Langdon, Moutain View; Joanne Otsuki, Oakland; David R. Buscaglia, Davis; Samuel H. King, San Jose, all of Calif.

[73] Assignee: Acuson Corporation, Mountain View, Calif.

[21] Appl. No.: 739,112

[22] Filed: Oct. 25, 1996

[51] Int. Cl.[6] .................................................. A61B 5/06
[52] U.S. Cl. .................................... 600/454; 73/861.25
[58] Field of Search .................................. 600/453–458; 73/861.25

[56] References Cited

U.S. PATENT DOCUMENTS

| | | |
|---|---|---|
| 4,109,642 | 8/1978 | Reid et al. . |
| 4,205,687 | 6/1980 | White et al. . |
| 4,452,082 | 6/1984 | Miwa . |
| 4,575,799 | 3/1986 | Miwa et al. . |
| 4,608,993 | 9/1986 | Albert . |
| 4,848,354 | 7/1989 | Angelsen et al. ..................... 73/861.25 |
| 4,905,206 | 2/1990 | Nishiyama et al. . |
| 4,932,415 | 6/1990 | Angelsen et al. . |
| 5,065,764 | 11/1991 | Nakamura et al. .................. 73/861.25 |
| 5,271,404 | 12/1993 | Corl et al. . |
| 5,287,753 | 2/1994 | Routh et al. .......................... 73/861.25 |
| 5,553,620 | 9/1996 | Snider et al. . |
| 5,582,176 | 12/1996 | Swerling et al. . |
| 5,606,972 | 3/1997 | Routh ................................. 128/661.09 |
| 5,628,321 | 5/1997 | Scheif et al. ........................ 600/454 X |
| 5,634,465 | 6/1997 | Schmiesing et al. ................ 73/861.25 |
| 5,647,366 | 7/1997 | Weng ................................. 128/661.09 |

FOREIGN PATENT DOCUMENTS

| | | |
|---|---|---|
| 0 172 687 A3 | 2/1986 | European Pat. Off. . |
| 3605 194 A1 | of 0000 | Germany . |
| 2-1779465 | 7/1990 | Japan . |
| 3-188841 | 8/1991 | Japan . |

OTHER PUBLICATIONS

Liv Hatle, M.D., et al., Doppler Ultrasound in Cardiology, Physical Principles and Clinical Applications, pp. 59–62, 1982.

"Analysis of the Hepatic Hemodynamics Using an Ultrasonic Duplex System", Fuminori Moriyasu, et al.; Jpn J Med Ultrasonics, vol. 12, No.1, (1985), pp. 55–61, (abstract and Figures).

"Measurement of the Superior Mesenteric Artery Flow Using an Ultrasonic Pulsed Doppler Duplex System", Takefumi Nakamura, et al.; Jpn J Med Ultrasonics, vol. 12, No. 2, (1985), pp. 55–63, (abstract and Figures).

"Spectral analysis of Doppler signals and computation of the normalised first moment in real time using a digital signal processor", F.S. Schlindwein, et al., Medical & Biological Engineering & Computing, Mar. 1988, pp. 228–232.

"Real–Time system for robust spectral parameter estimation in Doppler signal analysis", C. Di Giuliomaria, et al., Medical & Biological Engineering & Computing, Jan. 1990, pp. 54–59.

(List continued on next page.)

Primary Examiner—Francis J. Jaworski
Attorney, Agent, or Firm—Craig A. Summerfield; Brinks, Hofer, Gilson & Lione

[57] ABSTRACT

A method for interactively detecting a maximum velocity from acquired echo signals in an ultrasound system is provided. A processor with maximum velocity code is provided. The code has a variable. A user input provides a value for the variable while the ultrasound system is in a maximum velocity mode. The ultrasound system is operated in a maximum velocity mode. The echo signals are processed to determine said maximum velocity, and the processing is adjusted while remaining in said maximum velocity mode. During CINE playback, delimeters are generated for adjusting the time period of parameter calculation.

86 Claims, 8 Drawing Sheets

Microfiche Appendix Included
(6 Microfiche, 509 Pages)

OTHER PUBLICATIONS

"Calculation of Cardiac Output Using Multigate Doppler Echocardiography", Gengi Satomi, et al., Jpn J Med Ultrasonics, vol. 17, No. 5, 1990 pp. 11–16, (summary, abstract and Figures).

"An Investigation of Simulated Umbilical Artery Doppler Waveforms. I. The Effect of Three Physical Parameters on the Maximum Frequency Envelope and on Pulsatility Index", P.R. Hoskins, et al., Ultrasound in Medicine & Biology, vol. 17, No. 1, 1991, pp. 7–21.

"Portable directional ultrasonic Doppler blood velocimeter for ambulatory use", N. Dahnoun, et al., Medical & Biological Engineering & Computing, Sep. 1990, pp. 474–482.

"Continuous Doppler Sonography: The Technical Fundamentals For Clinical Long Term Monitoring", B. Bressler, et al., Proceedings of the Annual International Conference of the IEEE Engineering in Medicine and Biology Society, vol. 13, No. 4, 1991, pp. 1626, 1627.

"Mean or maximum velocity using pulsed Doppler ultrasound in determination of Doppler–derived cardiac output in the newborn infant", H. Hirsimäki, et al., Medical & Biological Engineering & Computing, Jan. 1993, pp. 58–60.

"Versatile microcomputer–based system for the capture, storage and processing of spectrum–analysed Doppler ultrasound blood flow signals"; D.R. Prytherch, et al., Medical & Biological Engineering & Computing, Sep. 1985, pp. 445–452.

J.Y. David, S.A. Jones, & D.P. Giddens—Modern Spectral Analysis Techniques For Pulsed Doppler Ultrasound Velocity Measurements, *Proceedings of the Sixteenth Annual Northeast Bioengineering Conference*, 1990.

M.S. Kassam, R.S.C. Cobbold, K.W. Johnston and C.M. Graham—Method for Estimating The Doppler Mean Velocity Waveform, Ultrasound in Med. & Biol., 1982.

Liv Hatle, M.D. et al., Doppler Ultrasound in Cardiology, Physical Principles and Clinical Applications, pp. 59–62, 1982.

R.W. Gill, Performance of the Mean Frequency Doppler Modulator, Ultrasound in Med. & Biol., vol. 5, pp. 237–247, 1979.

Levy Gerzberg, et al, Power–Spectrum Centroid Detection for Doppler Systems Applications, Ultrasonic Imaging 2, pp. 232–261, 1980.

Levy Gerzberg, et al., The $\sqrt{7I}$ Power–Spectrum Centroid Detector: System Considerations, Implementation, and Performance, Ultrasonic Imaging 2, pp. 262–289, 1980.

K.W. Johnston, et al., Online Identifying and Quantifying Doppler Ultrasound Waveforms, Med. & Biol. Eng. & Comput., pp. 336–342, May 1982.

T. D'Alessio, 'Objecitve $\propto$ Algorithm for Maximum Frequency Estimation in Doppler Spectral Analyses, Med. & Biol. Eng. & Comput., pp. 63–68, Jan. 1985.

Larry Y. L. Mo., et al., Comparison of Four Digital Maximum Frequency Estimators For Doppler Ultrasound, Ultrasound in Med. & Biol., vol. 14, No. 5, pp. 355–363, 1988.

A. Heringa, et al., Computer Processing of Cardiac Doppler Signals, Med. & Biol. Eng. & Comput. pp. 147–152, Mar. 1988.

D.H. Evans, et al., Doppler Ultrasound, Physics, Instrumentation, and Clinical Applications, pp. 166–269, 1989.

Guy Cloutier, et al., Computer Evaluation of Doppler Spectral Envelope Area in Patients Having a Valvular Aortic Stenosis, Ultrasound in Med. & Biol., vol. 16, No. 3, pp. 247–260, 1990.

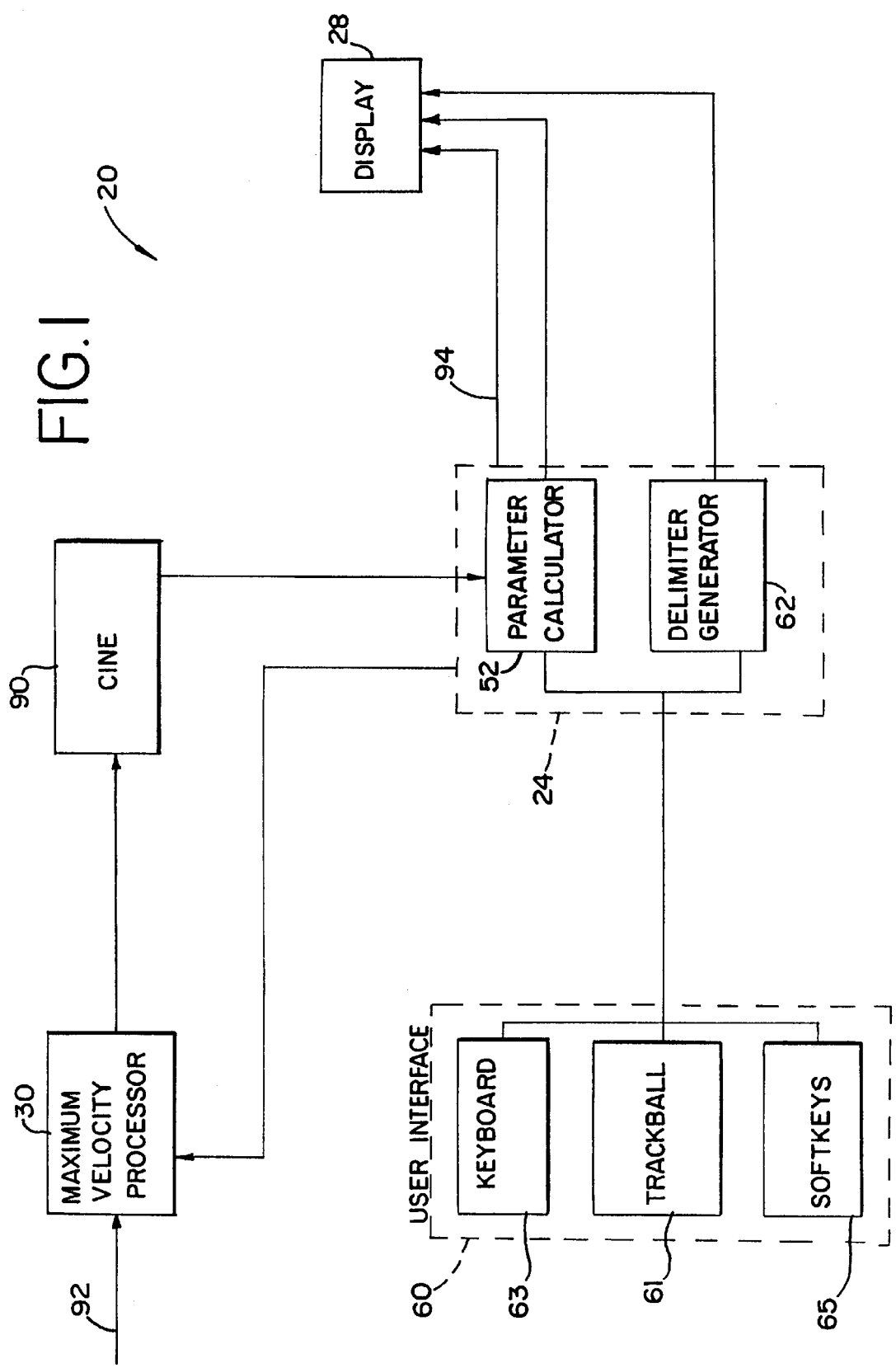

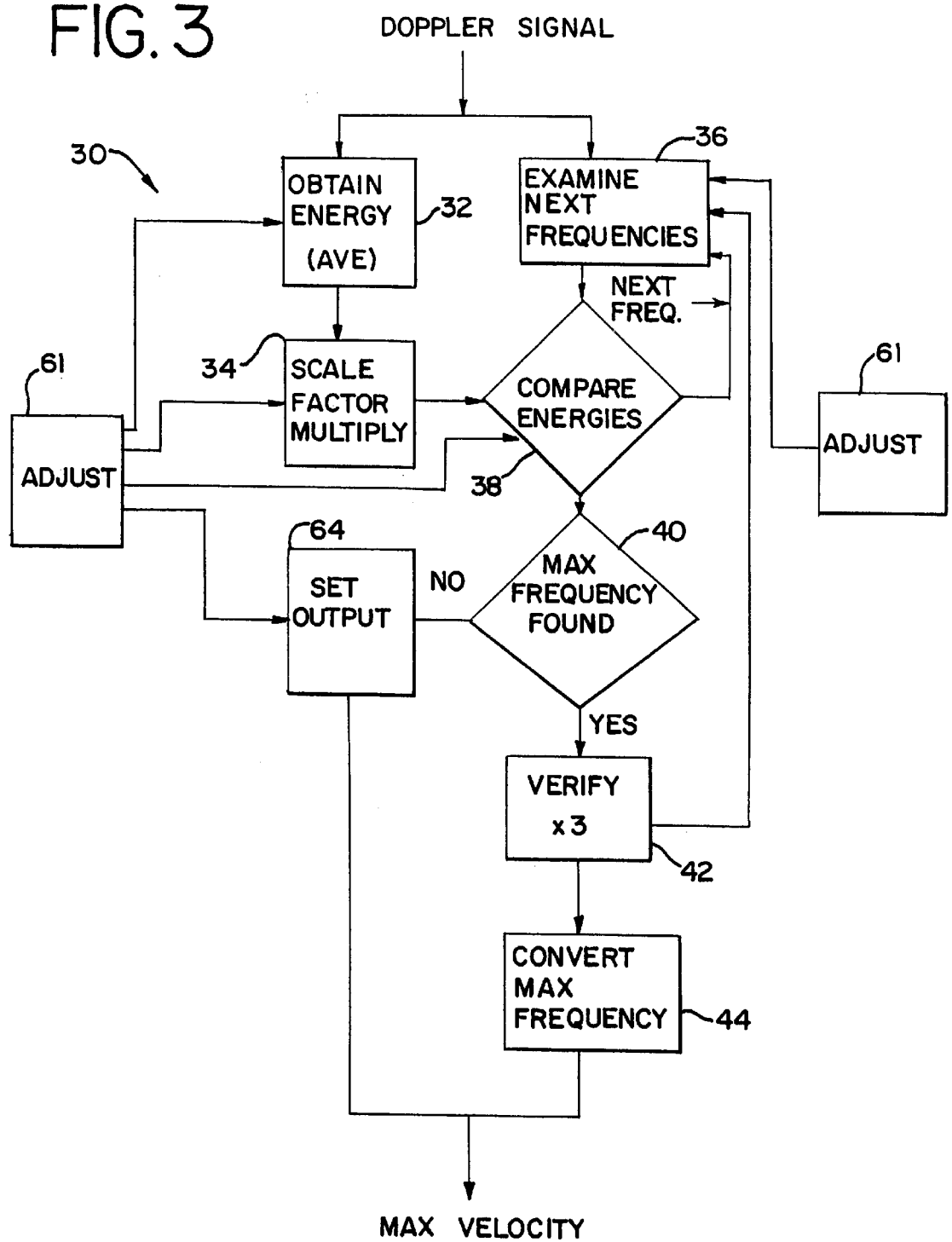

FIG. 4

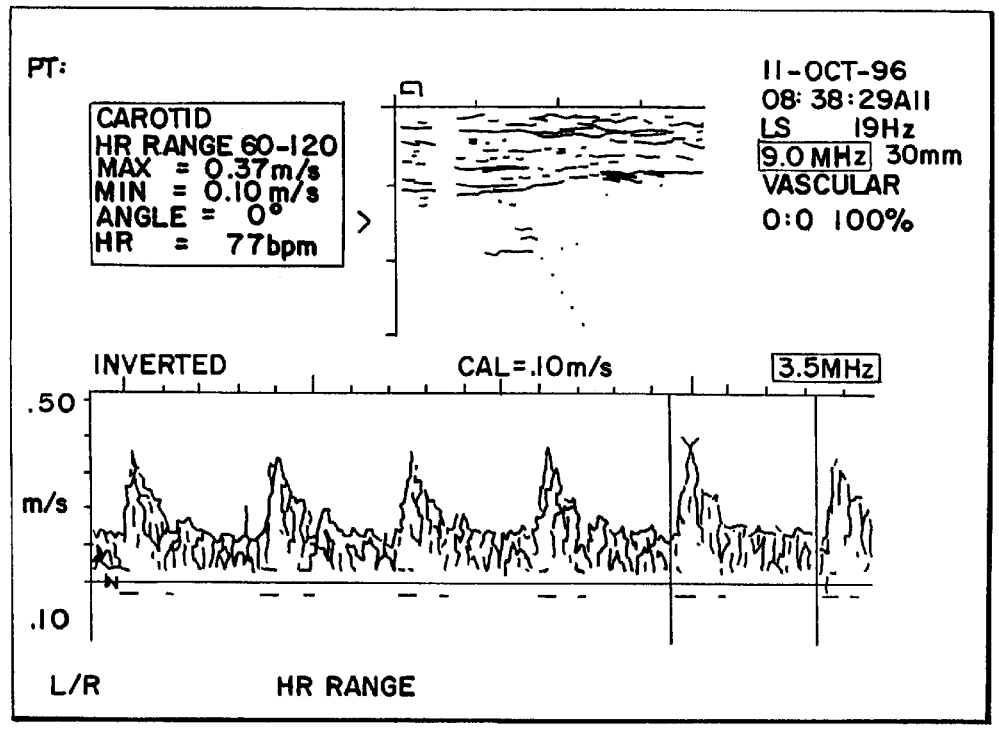

FIG. 5A

```
            AUTO-DOPPLER CONFIGURATION
            CONFIGURATION NAME:  CONFIG I
                    NUMBER OF SITES: 1
                    SIGNAL TYPE:    HIGH VOLUME
                                    HIGH VOLUME
                                    LOW RESISTANCE  ROZEN
    MAXIMUM VELOCITY            M   TRIPHASIC       OFF
    MINIMUM VELOCITY            M   CARDIOLOGY      OFF
    DOPPLER FLOW ANGLE              ANGLE    OFF    OFF
    TIME-AVERAGED MAX VEL.          TAMX     OFF    OFF
    HEART RATE                      HR       OFF    OFF
    ACCELERATION                    ACCEL    OFF    OFF
    PULSATILITY INDEX               PI       OFF    OFF
    RESISTIVITY INDEX               RI       OFF    OFF
    SYSTOLIC/DIASTOLIC RATIO        S/D      OFF    OFF
    VELOCITY-TIME INTEGRAL          VTI      OFF    OFF
    EJECTION TIME                   ET       OFF    OFF
    ACCELERATION TIME               AT       OFF    OFF
    MEAN GRADIENT                   MnGRD    OFF    OFF
    PEAK GRADIENT                   PkGRD    OFF    OFF
    CARDIAC OUTPUT                  CO       OFF    OFF

PRIOR MENU      IMAGE                       "SHOW MENU
```

FIG. 5B

```
              AUTO-DOPPLER CONFIGURATION
              CONFIGURATION NAME: CAROTID
                        NUMBER OF SITES: 8
                        SIGNAL TYPE: HIGH VOLUME
                                              LIVE   FROZEN
   MAXIMUM VELOCITY          MAX              [ON]    ON
   MINIMUM VELOCITY          MIN               ON     ON
   DOPPLER FLOW ANGLE        ANGLE             ON     ON
   TIME-AVERAGED MAX VEL.    TAMX              OFF    OFF
   HEART RATE                HR                ON     ON
   ACCELERATION              ACCEL             OFF    OFF
   PULSATILITY INDEX         PI                OFF    OFF
   RESISTIVITY INDEX         S/D               OFF    OFF
   SYSTOLIC/DIASTOLIC RATIO  S/D               OFF    OFF
   VELOCITY-TIME             VTI               OFF    OFF
   EJECTION TIME             ET                OFF    OFF
   ACCELERATION TIME         AT                OFF    OFF
   MEAN GRADIENT             MnGRD             OFF    OFF
   PEAK GRADIENT             PkGRD             OFF    OFF
   CARDIAC OUTPUT            CO                OFF    OFF

PRIOR MENU      IMAGE                       "OFF/ [ON]
```

FIG. 5C

```
              CONFIGURATION NAME: RENAL
                        NUMBER OF SITES: 2
                        SIGNAL TYPE: LOW RESISTANCE
                                              LIVE   FROZEN
   MAXIMUM VELOCITY          MAX              [ON]    ON
   MINIMUM VELOCITY          MIN               ON     ON
   DOPPLER FLOW ANGLE        ANGLE             ON     ON
   TIME-AVERAGED MAX VEL.    TAMX              OFF    OFF
   HEART RATE                HR                ON     ON
   ACCELERATION              ACCEL             OFF    OFF
   PULSATILITY INDEX         PI                OFF    OFF
   RESISTIVITY INDEX         RI                OFF    OFF
   SYSTOLIC/DIASTOLIC RATIO  S/D               OFF    OFF
   VELOCITY-TIME INTEGRAL    VTI               OFF    OFF
   EJECTION TIME             ET                OFF    OFF
   ACCELERATION TIME         AT                OFF    OFF
   MEAN GRADIENT             MnGRD             OFF    OFF
   PEAK GRADIENT             PkGRD             OFF    OFF

PRIOR MENU      IMAGE                       "OFF/ [ON]
```

FIG. 5D

```
        AUTO-DOPPLER CONFIGURATION
        CONFIGURATION NAME: OVARIES
              NUMBER OF SITES: 2
              SIGNAL TYPE: LOW RESISTANCE
                                     LIVE  FROZEN
  MAXIMUM VELOCITY          MAX      [ON]   ON
  MINIMUM VELOCITY          MIN       ON    ON
  DOPPLER FLOW ANGLE        ANGLE     ON    ON
  TIME-AVERAGED MAX VEL.    TAMX      OFF   OFF
  HEART RATE                HR        ON    ON
  ACCELERATION              ACCEL     OFF   OFF
  PULSATILITY INDEX         PI        OFF   OFF
  RESISTIVITY INDEX         RI        OFF   OFF
  SYSTOLIC/DIASTOLIC RATIO  S/D       OFF   OFF
  VELOCITY-TIME INTEGRAL    VTI       OFF   OFF
  EJECTION TIME             ET        OFF   OFF
  ACCELERATION TIME         AT        OFF   OFF
  MEAN GRADIENT             MnGRD     OFF   OFF
  PEAK GRADIENT             PkGRD     OFF   OFF
  CARDIAC OUTPUT            CO        OFF   OFF

PRIOR MENU      IMAGE                 "OFF/[ON]
```

FIG. 5E

```
        AUTO-DOPPLER CONFIGURATION
        CONFIGURATION NAME: TRI-PHASIC
              NUMBER OF SITES: 2
              SIGNAL TYPE: TRIPHASIC
                                     LIVE  FROZEN
  MAXIMUM VELOCITY          MAX      [ON]   ON
  MINIMUM VELOCITY          MIN       ON    ON
  DOPPLER FLOW ANGLE        ANGLE     ON    ON
  TIME-AVERAGED MAX VEL.    TAMX      OFF   OFF
  HEART RATE                HR        ON    ON
  ACCELERATION              ACCEL     OFF   OFF
  PULSATILITY INDEX         PI        OFF   OFF
  RESISTIVITY INDEX         RI        OFF   OFF
  SYSTOLIC/DIASTOLIC RATIO  S/D       OFF   OFF
  VELOCITY-TIME INTEGRAL    VTI       OFF   OFF
  EJECTION TIME             ET        OFF   OFF
  ACCELERATION TIME         AT        OFF   OFF
  MEAN GRADIENT             MnGRD     OFF   OFF
  PEAK GRADIENT             PkGRD     OFF   OFF
  CARDIAC OUTPUT            CO        OFF   OFF

PRIOR MENU      IMAGE                 "OFF/[ON]
```

FIG. 5F

```
              AUTO-DOPPLER CONFIGURATION
            CONFIGURATION NAME: LVOT
                        NUMBER OF SITES: LVOT
                        SIGNAL TYPE: CARDIOLOGY
                                        LIVE  FROZEN
    MAXIMUM VELOCITY         MAX        [ON]   ON
    MINIMUM VELOCITY         MIN         OFF   OFF
    DOPPLER FLOW ANGLE       ANGLE       OFF   OFF
    TIME-AVERAGED MAX VEL.   TAMX        OFF   OFF
    HEART RATE               HR          ON    ON
    ACCELERATION             ACCEL       OFF   OFF
    PULSATILITY INDEX        PI          OFF   OFF
    RESISTIVITY INDEX        RI          OFF   OFF
    SYSTOLIC/DIASTOLIC RATIO S/D         OFF   OFF
    VELOCITY-TIME INTEGRAL   VTI         ON    ON
    EJECTION TIME            ET          OFF   OFF
    ACCELERATION TIME        AT          OFF   OFF
    MEAN GRADIENT            MnGRD       ON    ON
    PEAK GRADIENT            PkGRD       ON    ON
    CARDIAC OUTPUT           CO          ON    ON

PRIOR MENU     IMAGE                      "OFF/[ON]
```

FIG. 6

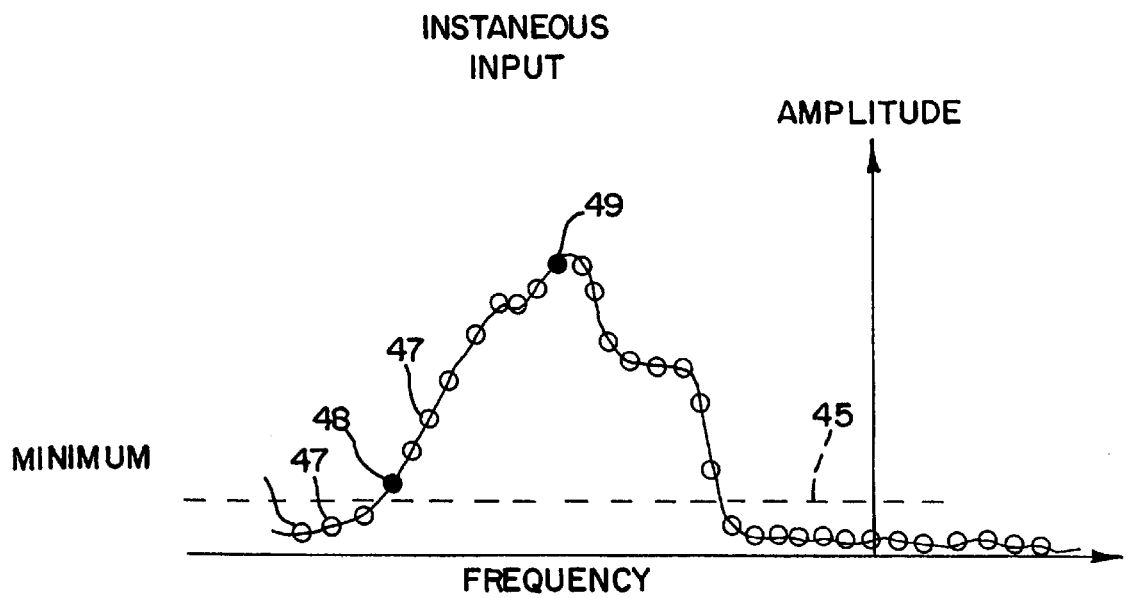

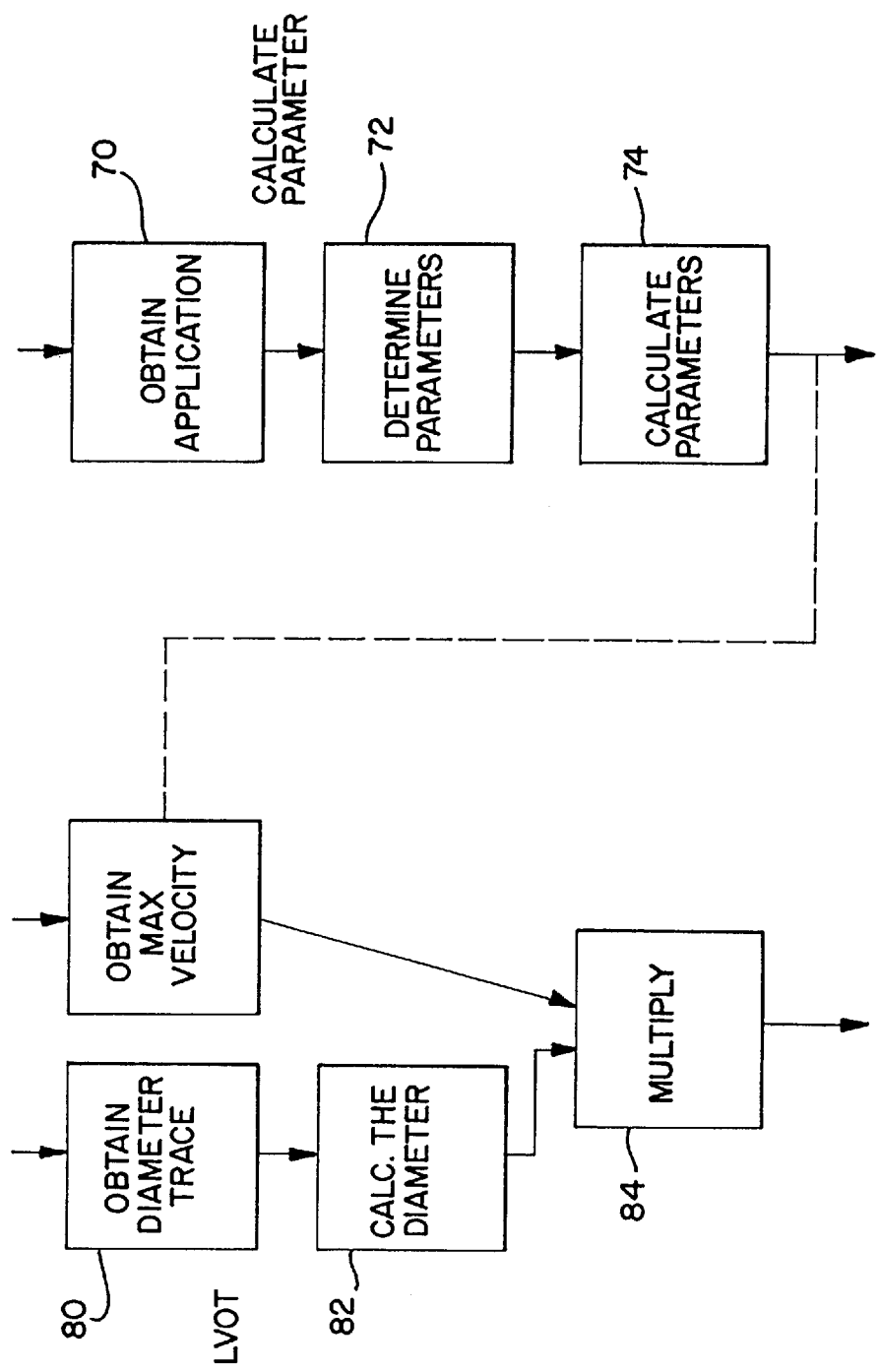

INTERACTIVE DOPPLER PROCESSOR AND METHOD

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

This application includes one microfiche appendices. The appendices contain six microfiche with 509 frames.

FIELD OF THE INVENTION

This invention relates in general to ultrasound systems and in particular to a system for detecting and displaying maximum velocity using spectral Doppler techniques.

BACKGROUND OF THE INVENTION

Ultrasound imaging systems detect and display Doppler shifts of returning echoes. The Doppler shifts represent blood flow patterns. Spectral Doppler is one known ultrasound technique to display blood flow patterns associated with a point in a body.

In spectral Doppler, an ongoing series of Doppler spectra are displayed. Each spectrum represents a point in time and a range of frequencies of the spectrum. The frequencies are proportional to blood flow velocities. The signal strength of each frequency is displayed on the spectrum as a brightness. Generally, certain frequencies in the spectrum are due to noise and not blood flow. These noise related frequencies typically have a small amplitude.

Such an ongoing series of Doppler spectra can be used to measure blood flow characteristics. Many of these characteristics depend on the maximum blood flow velocity throughout the heart cycle. Conventionally, the operator hand-traces maximum velocity on a frozen Doppler strip, or spectral display. For each spectrum, the operator manually determines the highest velocity not caused by noise. Various parameters are then calculated from the maximum velocity curve, such as pulsivity index.

Some ultrasound systems automate the maximum velocity curve determination. Typically, an algorithm is applied to each spectrum to obtain the highest frequency signal not related to noise. Different algorithms have been developed for detecting maximum flow in the presence of noise. For example, Hatle et al., "Doppler Ultrasound in Cardiology," $2^{nd}$ Edition, demonstrates the use of a multiple moving windows to determine a maximum frequency for each spectrum.

D'Alessio, "Objective algorithm for maximum frequency estimation in Doppler spectral analyzers", Med. & Bio. Eng'g & Computing, 1985, pgs. 23, 63–68, demonstrates another technique for determining the maximum frequency for each spectrum. D'Alessio obtains the energy associated with the highest negative or positive frequency signal. The energy is multiplied by a scale factor to create a minimum signal energy threshold. The highest positive or negative frequency with an energy above the minimum signal energy threshold is selected as the maximum frequency. The maximum frequency is converted to a maximum velocity. A maximum velocity curve is obtained by repeating the determination of the maximum velocity for each of multiple ongoing spectra.

The algorithms discussed above have one or more constants. The maximum velocity is a function of the constants. The constants are either set by the design of the ultrasound machine or are set by the operator as part of a set-up function.

One ultrasound machine may be used for many applications, such as examination of different disease states or locations in a body. However, none of the ultrasound systems for obtaining and displaying ultrasound data is entirely satisfactory for each application. It is therefore desirable to provide an improved ultrasound system for obtaining and displaying ultrasound data.

SUMMARY OF THE INVENTION

The invention provides an efficient method for processing and displaying various ultrasound data. In one aspect, a method for interactively detecting a maximum velocity from acquired echo signals in an ultrasound system is provided. A processor with maximum velocity code is provided. The code has a variable. A user input provides a value for the variable while the ultrasound system is in a maximum velocity mode. The ultrasound system is operated in a maximum velocity mode. The echo signals are processed to determine said maximum velocity, and the processing is adjusted while remaining in said maximum velocity mode.

In another embodiment, the maximum velocity is displayed. As the maximum velocity is processed, user input alters the processing in real time.

In another aspect of the invention, the processor contains configuration code and maximum velocity code. The configuration code has multiple configuration data and the maximum velocity code has the variable. A user input provides data to select at least one of the multiple configuration data to adjust the processing of the maximum velocity. The configuration data provides a value for the variable. The echo signals are processed to determine the maximum velocity.

In yet another aspect of the invention, an apparatus for providing cardiac output from echo signals in an ultrasound system is provided. A processor has maximum velocity code for determining a maximum velocity. A user input is operatively connected to the processor for providing diameter input data. A multiplier multiplies the diameter input data with the maximum velocity to obtain a measurement indicative of cardiac flow.

In another aspect of the invention, an apparatus for interactively selecting a time period for calculation of at least one parameter from echo signals in a CINE playback mode of an ultrasound system is provided. A waveform is displayed on a display. A first and second moveable delimiter are also displayed on the display. A user input provides delimiters position data to a processor. The processor calculates the parameter as a function of the delimiter position data.

BRIEF DESCRIPTION OF THE DRAWINGS

FIG. 1 is a block diagram illustrating selected portions of a spectral Doppler ultrasound system.

FIG. 3 is a flow diagram of a maximum velocity algorithm.

FIG. 4 is a display screen generated by the spectral Doppler ultrasound system of FIG. 1.

FIG. 5A is an configuration menu screen showing multiple signal types and multiple parameters for user selection.

FIG. 5B is an configuration menu screen for a carotid configuration.

FIG. 5C is an configuration menu screen for a renal configuration.

FIG. 5D is an configuration menu screen for an ovaries configuration.

FIG. 5E is an configuration menu screen for a Tri-phasic configuration.

FIG. 5F is an configuration menu screen for a LVOT configuration.

FIG. 6 is a graphical representation of an echo signal with sample points.

FIG. 7 is a flow chart demonstrating the calculation of parameters, including cardiac outflow.

DETAILED DESCRIPTION OF PREFERRED EMBODIMENTS

Referring now to the Figures, and in particular FIG. 1, a portion of an ultrasound system is generally shown at 20. Preferably the ultrasound system includes a spectral Doppler system, such as a pulse wave, continuous wave or auxiliary continuous wave system, as known in the art. Generally, spectral Doppler systems detect, process and display information based on echo signals.

Prior to detecting and processing any echo signals, microprocessor 24 controls any initial setup of the ultrasound system. Once the ultrasound system is setup, the user may operate the system to process echo signals. For example, the ultrasound system is placed in a maximum velocity mode. In the maximum velocity mode, the ultrasound system processes echo signals to display a two-dimensional image screen or determine a maximum velocity. The user may select a point or line on the two-dimensional image screen for further spectral Doppler processing.

Spectral Doppler processing is performed by the ultrasound system. A portion of the ultrasound system is not shown in FIG. 1. The portion not shown generally comprises a transmitter that produces a signal. The signal is applied to a body by a transducer. The transducer detects echo signals resulting from the applied signal. A beamformer receives the echo signals and places the echo signals on line 92.

The portion 20 of the ultrasound system shown in FIG. 1 is discussed below. The detected echo signals are provided to maximum velocity processor 30 on line 92. Preferably, maximum velocity processor 30 is a digital signal processor. Maximum velocity processor 30 creates data for spectral display 23 (FIG. 2B) as known in the art and determines a maximum velocity.

Referring to FIG. 2, spectral display 23 represents an ongoing series of Doppler spectra. The Doppler spectra are derived from the detected echo signals and displayed as a Doppler spectral strip.

Figure 2A:
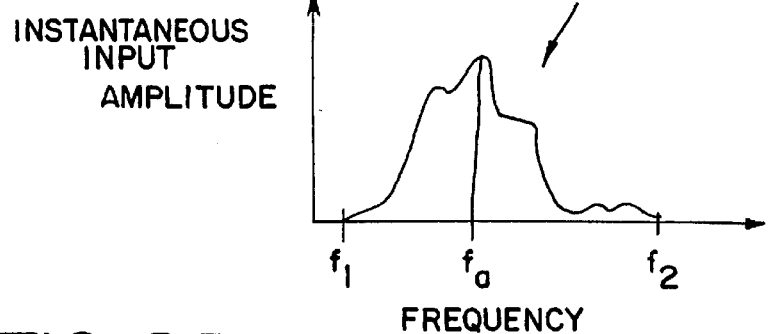
FIG. 2A is a graphical representation of an echo signal.

The display of the spectra is based on multiple characteristics of the echo signals. As shown in FIG. 2A, a Doppler spectrum comprises the signal strength, a function of either an amplitude or energy, of the detected echo signals as a function of frequency. The frequencies range from positive to negative frequencies. Positive frequencies correspond to blood flow away from the transducer, and negative frequencies correspond to blood flow towards the transducer. The greater the frequency, either negative or positive, the greater the blood flow velocity. A baseline frequency represents the frequency at which blood flow is zero.

Referring to FIG. 6, a Doppler spectrum, as used by the ultrasound system, is preferably formed from a series of sample points 47. Sample points 47 are detected as discussed above and preferably digitized as known in the art. Each sample point has a frequency and a signal strength. The frequency of each sample point 47 corresponds to either a positive frequency, a negative frequency or the baseline frequency. In this example, 128 frequencies and the corresponding signal strengths are sampled, though other numbers of frequencies could be used.

Figure 2B:
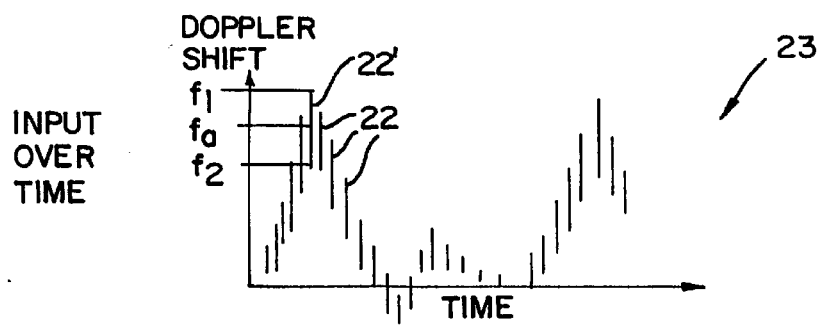
FIG. 2B is a graphical representation of a spectral Doppler output display.

Referring to FIGS. 1, 2B and 6, the sample point 47 information for spectral display 23 is then passed through or stored in CINE 90 which preferably is a microcontroller but as known in the art, other types of memory devices may be used. CINE 90 stores the data for spectral display 23 for later playback. As known in the art, CINE 90 outputs the data for spectral display either in a playback mode or in real time. The data for spectral display 23 is then scan converted (not shown) and passed to microprocessor 24.

The data for spectral display 23 is caused to be displayed on display 28 by microprocessor 24. Preferably, microprocessor 24 is a general purpose microprocessor, such as Motorola 68K family of processors. Microprocessor 24 controls release of information from CINE 90 and display 28. Other microprocessors and configurations for obtaining the spectral display 23 may be used As shown in FIG. 2B and as known in the art, the sample points 47 contained in a sequence of Doppler spectra are used to create the spectral display 23. Spectral display 23 includes a series of spectral lines 22. Each spectral line 22 represents the range of frequencies measured at a single respective time. The range of frequencies are referenced to the vertical axis. For example, spectral line 22' may correspond to the echo signals of FIG. 2A. The highest frequency, $F_2$, on the horizontal frequency axis of FIG. 2A corresponds to the highest frequency, $F_2$, of spectral line 22' on the vertical frequency axis of FIG. 2B.

The signal strength associated with each frequency is displayed as a brightness on the spectral line 22. A high signal strength portion of the signal will correspond to a bright point on spectral line 22. In this example, the point on spectral line 22' corresponding to frequency $f_a$ is the brightest. As shown on FIG. 2A, the signal strength is highest for frequency $f_a$. Lower signal strength frequencies will have lesser brightness on line 22. Thus, ultrasound system 20, as shown by FIG. 2B, provides frequency range with qualitative signal strength information for each spectral line 22.

The provided spectral line 22 information is obtained as a function of time to create spectral display 23. Spectral display 23 is preferably a display of velocity and signal strength over time. The frequencies of spectral lines 22 are converted as known in the art to velocities. Alternatively, frequencies can be displayed. In the example of FIG. 2B, the brightness of each point on spectral line 22 is based on amplitude, which is proportional to the square root of energy. Alternatively, the brightness can be based on energy.

Figure 2C:
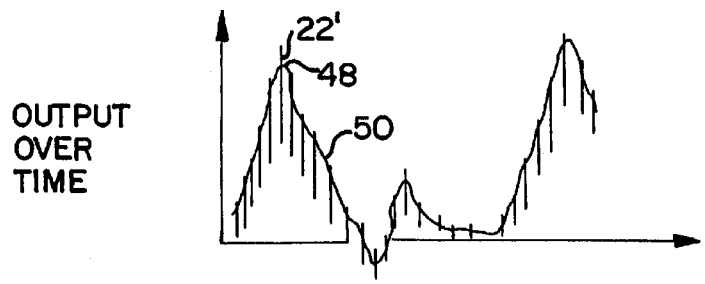
FIG. 2C is a graphical representation of the display of FIG. 2B with an overlaid maximum velocity curve.
Figure 2D:
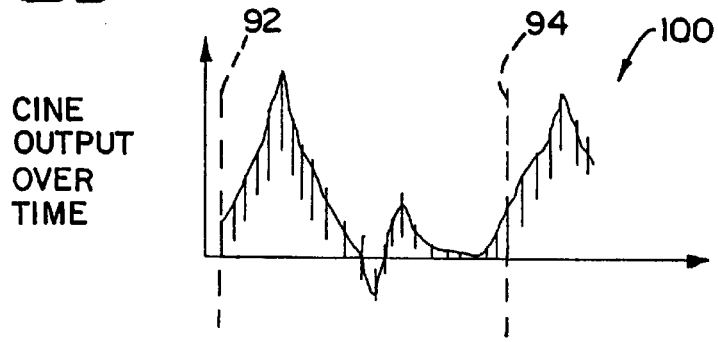
FIG. 2D is a graphical representation of a frozen spectral Doppler output display based on CINE playback.

Along with creating spectral display 23, ultrasound system 20 also determines a maximum Doppler velocity for each spectral line 22. Referring to FIGS. 1 and 2C, microprocessor 24 causes CINE 90 to plot the maximum velocity point 48 on spectral display 23. A maximum velocity point 48 for each spectral line is determined. Thus, a maximum velocity curve 50 is obtained. The data representing maximum velocity curve 50 is passed to microprocessor 24.

The maximum velocity is determined from each spectrum. Generally, the characteristics of each spectrum are attributable to both noise and blood flow. The maximum velocity corresponds to the highest frequency attributable to blood flow. As known in the art, an algorithm is applied to each spectral line to determine the maximum velocity. Referring to FIG. 1, maximum velocity processor 30 applies the algorithm. Other implementations for algorithm 30 may be used, such as hard wiring or different processors.

Referring to FIG. 6, the algorithm distinguishes between those sample points 47 which are associated with noise and those which are associated with blood flow. Preferably, the algorithm is derived from the algorithm suggested by D'Alessio. Other maximum velocity algorithms can be used, such as the Hattle algorithm. The preferred algorithm operates as shown in the block diagram of FIG. 3.

Referring to FIG. 3, in block 32, the sample points 47 (FIG. 6) of a spectrum are examined for the largest positive frequency. Alternatively, the largest negative frequency or both the largest negative and positive frequencies can be used. Preferably, multiple sample points 47 (FIG. 6) with the highest frequencies are examined. The noise bias variable in the attached microfiche appendix provides the preferred number of highest frequencies examined. The signal strengths associated with the multiple largest positive frequency sample points are then obtained, as represented by block 32. As shown by block 32, the obtained signal strengths are averaged. The average signal strength is multiplied by a scale factor in block 34.

The scale factor is selected to differentiate noise related signals from blood flow related signals. The result of the scale factor and averaged signal strength multiplication generally comprises a signal to noise ratio. The scale factor is selected based on empirical experience. Thus, the signal to noise ratio varies with the application.

The signal to noise ratio is used as a minimum non-noise signal threshold. The minimum non-noise threshold signal is represented by dashed line 45 in FIG. 6. Further, the minimum non noise signal threshold may be an average of minimum non-noise signal thresholds from multiple spectra. For example, every fifth spectrum may be examined to determine a minimum non-noise signal threshold. Each new value is averaged with previous values. The rate of examination is given in the microfiche code as the noise signal sampler rate variable. Further, the number of most recently sampled spectra included in the averaged value is given in the attached microfiche appendix as the noise buffer length variable.

The minimum non-noise threshold determined above is compared to a set threshold in block 34. If the minimum non-noise signal threshold is less than the set threshold, the set threshold is used as the minimum non-noise signal threshold. The set threshold may be varied. The set threshold is provided in the microfiche appendix as the noise threshold value.

The minimum non-noise signal threshold is then applied to signal strengths from other sample points 47 (FIG. 6) in block 38. The frequencies of the sample points 47 (FIG. 6) are examined at block 36 from the frequency furthest from the baseline frequency towards the baseline frequency. For each frequency examined, the corresponding signal strength is compared to the minimum non-noise signal threshold, at block 38. As demonstrated by the next frequency line, multiple frequencies and associated signal strengths are examined and compared. This loop continues until the first signal strength higher than the minimum non-noise signal threshold is found or all the frequencies have been examined. The first signal strength higher than the minimum non-noise signal threshold is considered the maximum frequency. Sample point 48 in FIG. 6 represents the sample point 47 corresponding to the maximum frequency. Referring back to FIG. 3, the frequency corresponding to this first signal strength represents the maximum frequency found at block 40.

Alternatively and preferably, the maximum frequency is checked for accuracy. The signal strength (second signal strength) associated with the next lowest frequency from the first frequency is also examined, once again represented by block 36. As discussed above, the first frequency corresponds to the highest frequency with a signal strength above the minimum non-noise signal threshold. This second signal strength is compared to the minimum non-noise signal threshold, once again represented by block 38. If the second signal strength is above the minimum non-noise signal threshold, then the maximum frequency has been verified.

Preferably, the signal strengths associated with the three next lowest frequencies are all verified to be above the minimum non-noise signal. The number of frequencies used for verification may vary and are provided by the consecutive bins variable in the code attached in the microfiche appendix. Thus, only the first frequency with a signal strength above the minimum non-noise signal threshold (sample point 48 in FIG. 6) which has three consecutive following frequencies with signal strengths above the minimum non-noise signal threshold is selected as a verified maximum frequency, as shown by block 42.

The maximum frequency is then converted to a velocity, as known in the art and represented by block 44. Also in block 44, various checks and limitations for the maximum velocity are performed. First, the maximum velocity is compared with the mean velocity of the spectrum. If the maximum velocity is not greater than the mean, an error message may be displayed. Whether to display the error message is enabled by the maximum greater than mean flag variable provided in the code in the microfiche appendix.

Second, the maximum velocity is compared to the maximum velocity of the previous spectrum in block 44. The comparison prevents unusual jumps in the maximum velocity from spectrum to spectrum in the event the difference between the maximum velocity and the previous maximum velocity is excessive. If the difference is greater than a maximum allowed jump, then the maximum allowed jump is added to the previous maximum velocity. The added value is then used as the maximum velocity for the current spectrum. The maximum allowed jump value is provided in the code attached as the microfiche appendix.

Finally, a low pass filter is also applied to the maximum velocity determination. The low pass filter acts to smooth out the maximum velocity curve 50 by removing high frequency variations. The more filtering provided, the less variable the maximum velocity. The values applied to filter the maximum velocity curve are provided as a median filter length variable in the attached microfiche appendix. Generally, the median filter length variable provides the number of consecutive maximum velocities to filer. Thus, block 44 represents output of a verified maximum velocity.

Referring back to FIG. 1, maximum velocity processor 30 outputs the maximum velocity to CINE 90 along with the spectral information for spectral display 23. CINE 90 stores each maximum velocity determined by maximum velocity processor 30. Thus, CINE 90 stores the maximum velocity curve 50. CINE 90 also passes the data corresponding to the maximum velocity curve 50 to microprocessor 24.

As known in the art, microprocessor 24 performs various calculations based on the maximum velocity curve 50. Microprocessor 24 includes parameter calculator 52 to perform the calculations. Parameter calculator 52 outputs the parameters to display 28. The parameters are displayed as quantities, as shown in FIG. 4. The available calculated parameters include: maximum velocity, minimum velocity, average height of the curve, pulsivity index, resistivity index, systole to diastole ratio, heart rate, acceleration, acceleration time, velocity time integral, cardiac output, ejection time, mean peak gradient, and peak gradient. Minimum velocity is the minimum value of the maximum velocity over a time period. Likewise, maximum velocity is the maximum value of the maximum velocity over a time period. Other calculations are also possible. The attached microfiche appendix contains the code for calculating the parameters in adcompute.c.

Parameter calculation and many of the other functions discussed above are conventional. The preferred embodiment of the present invention improves on the functions discussed above. These improvements are discussed below.

In the preferred embodiment, the parameters and maximum velocity displayed at any particular time depend on user input. User interface 60 provides input information to microprocessor 24. In particular, user interface 60 inputs information for use by parameter calculator 52 and maximum velocity processor 30. User interface 60 preferably includes a track ball device 61, a keyboard 63 and soft keys 65. Other user input devices may be used, such as a paddle switch. Preferably, keyboard 63 comprises a QWERTY keyboard and a dedicated key keyboard (hard keys). The soft keys 65 are keys provided for use with a corresponding reference on display 28. Thus, the function associated with depression of each of the soft keys 65 at any point in time is displayed next to the soft keys 65 on display 28.

User interface 60 allows the user to alter determination of the maximum velocity. Input from user interface 60 is provided to maximum velocity processor 30 via microprocessor 24. User adjustment of the maximum velocity determination occurs in real time just prior to or while processor 30 is determining the maximum velocity. Thus, user adjustment is made while the ultrasound system is in the maximum velocity mode.

The maximum velocity processor 30 applies the user input data as a variable for calculating the maximum velocity 46. Thus, as additional spectral lines 22 and associated maximum velocities are determined, the user can fine tune the maximum velocity. The user can examine the tuning changes on the qualitative spectral display 23. Any parameters are then calculated from user fine tuned maximum velocity curve 50.

The maximum velocity curve 50 is fine-tuned by adjusting the scale factor. Referring to FIG. 3, the scale factor for multiplication in block 34 is represented by the formula: $S_f = e^{0.02Pln(Sn)}$. $S_f$ is the applied scale factor. P is a percentage controlled by the user. $e^{0.02Pln(Sn)}$ is the nominal scale factor typically applied in the D'Alessio algorithm where P equals 50%.

The user provides input to adjust P. Referring to FIG. 1, one of the soft keys 65 is used to toggle on a scale factor control. Referring now to FIG. 4, a value 31 of P is displayed on display 28. For example, a value of 100% is displayed. Preferably, a default 50% value is initially displayed. Referring back to FIG. 1, the user uses trackball 61 to adjust the value of P. As the spectral display of FIG. 2(c) and the maximum velocity curve are created, the user selects a value 31 for P.

Referring to FIG. 3, the scale factor represented by block 34 is adjusted based in part on the selected value for P. Block 61 represents user input to adjust the maximum velocity. Adjusting the scale factor results in an adjustment of the maximum velocity found, as represented in block 40. Thus, the user controls the automatic calculation of the maximum velocity point 48 and the maximum velocity curve 50 shown in FIG. 2C. Such control is done in real time with the determination of the maximum velocity point 48 (FIG. 6) and maximum velocity curve 50.

The user also provides input to adjust the nominal scale factor ($S_n$). The nominal scale factor is preferably in the range of 2.5 to 4.0. Preferably, adjustment of the scale factor depends on the configuration selected. In the code attached as the microfiche appendix, the nominal scale factor corresponds with the noise scale factor variable. Referring to FIGS. 1, 3 and 6, selection of the configuration is discussed below and generally corresponds with a particular type of medical application of ultrasound system 20 to a body.

The algorithm used by maximum velocity detector 30 is also adjustable in other ways by the user. The maximum velocity detector 30 examines one of three frequency groups of sample points 47 for the maximum frequency. The frequency groups are either sample points 47 with positive frequencies, negative frequencies or both positive and negative frequencies. Positive frequencies are distinguished from negative frequencies by reference to the baseline frequency. The user may select the frequency group of sample points 47 for application of the algorithm.

Either prior to processing of signals by maximum velocity processor 30 or during processing, the user is provided with the frequency group options on display 28. Soft keys 65 are used to select the frequency group. The user selected input is provided to maximum velocity processor 30 via microprocessor 24. Alternatively, selection of a configuration, as discussed below, selects the frequency group. In the code attached as the microfiche appendix, the frequency group selected corresponds to the search mode variable.

Referring to FIG. 3, the adjust block 61 represents selection of the frequency group. The selection is input into obtain energy block 32 and examine frequency block 36. Maximum velocity processor 30 (FIG. 1) will obtain the energy at block 32 from the frequency or frequencies with the highest positive value(s), the energy from the frequency or frequencies with the highest negative value(s) or both such energies. The energy obtained depends on the user input information. The energy is multiplied by the scale factor. Further, maximum velocity processor 30 will examine the energies of frequencies with the highest positive, highest negative or both for comparison at blocks 36 and 38 based on the selection user input information.

If the algorithm is applied to both negative and positive frequencies, a maximum velocity for the positive frequencies is obtained and a maximum velocity for the negative frequencies is obtained. The maximum velocity is then the maximum absolute value of the maximum positive frequency value and the maximum negative frequency value.

Selection of frequency groups provides useful control of the maximum velocity. For example, examination of the umbilical artery may require examination of both negative and positive frequencies. The umbilical artery may have triphasic blood flow. The blood flows in a positive direction for one portion of a heartbeat, then flows in a negative direction for another portion of the same heartbeat, and finally returns to positive flow for the remainder of the heartbeat. Thus, the maximum velocity and any parameters that are a function of the entire heartbeat preferably consider both positive and negative flow.

Alternatively, echo signals may be obtained from either the umbilical artery or vein. If the user desires to examine just the artery with its positive flow, the user selects application of the algorithm to positive frequencies. If the user desires examination of the umbilical vein with its negative flow, then the user selects application of algorithm to negative frequencies. Thus, certain blood flow conditions are isolated by selection of the frequency group.

The user also selects the default output of maximum velocity processor 30. This selection is shown by block 64 of FIG. 3. The output of maximum velocity processor 30 is selectable if no signal strengths above the minimum non-noise signal threshold are found. Block 61 represents the input of adjustment information. Referring to FIG. 1, based on input from user interface 60, the maximum velocity processor 30 varies the default output. The default output selection input is provided as part of the configuration selection as discussed below. Further, the failure mode variable in the attached microfiche appendix corresponds to the default output selection provided by microprocessor 24 to maximum velocity processor 30.

As the default output, either a zero order hold, a weighted mean, or the frequency corresponding to the baseline is selected as the maximum velocity. For zero order hold, the maximum velocity processor 30 outputs the same maximum velocity as the prior spectral line 22 (FIG. 2B). For a single spectral line 22, the weighted mean default output is calculated as the sum of frequencies multiplied by the associated signal strengths where the sum is divided by the sum of the signal strengths.

Referring to FIG. 3, selecting the default output, as represented by block 64, allows user control over the maximum velocity curve 50 (FIG. 2B). For example, the blood flow in flow resistance flow may experience non-flow periods. The user selects a configuration with the baseline frequency for the maximum velocity default output. When no signals are detected above the minimum non-noise signal threshold, the baseline frequency is used to determine the maximum velocity. Thus, a maximum velocity of zero is shown. Zero flow velocity conforms to the expected non-flow periods. Alternatively, cardiology signals may have fairly continuous flow. Thus, the maximum velocity will always correspond to some amount of flow. To show continuous flow, the user selects a configuration with the weighted mean or zero order hold default output.

The user can also control whether energy or amplitude is used by maximum velocity processor 30. Energy is proportional to the square of amplitude. Energy is believed to more closely correlate to real blood flow. A function of Amplitude is generally used to determine the brightness of points on spectral line 22. Preferably, energy is used without selection by the user. Referring to FIG. 3, the user may adjust obtain signal strength block 32 and compare signal strengths block 38 by providing input information. Adjustment is represented by block 61. The input information is provided as part of a configuration selection as discussed below. Referring back to FIG. 1, maximum velocity processor 30 either obtains an energy and compares energies to the scaled energy or obtains an amplitude and compares amplitudes to the scaled amplitude. Alternatively, selection of the configuration discussed below provides an input to select either energy or amplitude.

As discussed above, the user controls the maximum velocity processor 30 to alter the maximum velocity curve 50. If a different algorithm is applied by maximum velocity processor 30, different constants may be used. The user may provide input to adjust these different constants. Thus, the user may optimize other algorithms.

In addition to control of the determination of the maximum velocity curve 50, the user controls calculation of parameters by microprocessor 24. User interface 60 provides input information to the microprocessor 24 and to the parameter calculator 52. Actual heart rate calculation is an example. The user enters an estimated heart rate. Soft keys 65 are used to activate and display default estimated heart rates. For example, ranges of 60–80 and 70–100 are displayed. Using soft keys 65, the estimated heart rate is selected. For example, 60–80 is selected. Generally, the estimated heart rate is qualitatively derived from the maximum velocity curve 50 by the user. The estimated heart rate selected is provided to microprocessor 24.

Microprocessor 24 determines the actual heart rate using the estimated heart rate. The maximum velocity curve 50 is examined for repetitive peaks. For maximum velocity curves 50 associated with triphasic conditions, multiple peaks may occur in one heartbeat. If parameter calculator 52 bases the actual heart rate on the multiple peaks instead of a single peak, an erroneous heart rate may be determined. The estimated heart rate is used to avoid erroneous heart rate determinations.

In real time acquisition and display of each signals, the microprocessor 24 processes the maximum velocity curve 50 without attempting to detect a change of slope for a set time. The set time is determined by the lower end of the user selected estimated heart rate. In the example above, the lower end is 60 beats per minute. For the time period from the lower end to the higher end of the estimated heart rate, the microprocessor 24 both processes the maximum velocity curve 50 and examines the maximum velocity curve 50 for a change in slope. Each change in slope represents a peak. Once a peak is found, microprocessor repeats the timing process described above. Based on the peaks, the maximum velocity curve is divided into multiple portions. Each portion represents a heart beat. The heart rate algorithm may also determine portions of the heart cycle, such as the systole portion by finding peaks between the heart beat peaks. Preferably, the above discussed heart rate algorithm is used for real time calculation of the heart rate.

Another algorithm for obtaining the heart rate from the maximum velocity curve 50 is provided in "Online identifying and quantifying Doppler ultrasound waveforms" by Johnston et al., *Medical & Biological Eng'g & Computing*, May 1982, pgs. 336–342. Detecting the heart rate based on echo signals recorded and played back from CINE 90 is preferably based on the algorithm proposed by Johnston. Generally, a highest peak value is obtained. 200 ms on each side of the peak is excluded as the next highest peak is obtained. The highest five contiguous peaks are obtained and assumed to distinguish five heart beats. Lower level peaks distinguishing other heart cycle portions and the types of blood flow associated with the maximum velocity curve are then determined.

The user may select other parameters, including heart rate, for calculation and display. A list of parameters is shown in FIG. 5A.

Calculation of some parameters, such as cardiac output, are preferably based on a portion of the heart cycle. Microprocessor 24 only uses data representing a particular portion of the maximum velocity curve 50. For example, examination of blood flow at the LVOT may be of interest. The systole portion of a heart beat at the aorta comprises actual flow. The distal half of the heartbeat typically comprises noise and various flow turbulence. Thus, only the systole portion of the heartbeat is of interest. Only maximum velocity curve data for the systole portion is used to determine some parameters; such as the velocity time integral.

Other parameters are calculated over an entire heartbeat. For example pulsitility index is calculated over an entire heart cycle. The parameter calculator 52 uses the heart rate information calculated above. Thus, selection of some parameters for calculation generally requires calculation of the heart cycle even if heart cycle is not displayed.

The user selection of parameters and other adjustments discussed above may be simplified. Instead of selecting the parameters for display, the user selects the configuration. Configuration selection is done either before processing the echo signals or as the signals are processed and displayed. In either situation, configuration selection is done while the ultrasound system is in the maximum velocity mode and not in a set-up mode.

A menu is provided for configuration selection. For example, the menu of configurations may be presented on display 28. User interface 60 is used to select one of the configurations. Preferably, a hard key on keyboard 63 is used to activate configuration selection. Trackball 61 is used to move a highlight on the menu. Then, a soft key 65 is used to select the configuration. The selection is based on the region of the body being examined and the desired parameters for calculation. Display of the menu is either during echo signal processing or prior to processing of the maximum velocity curve 50.

Preferably, carotid, renal, ovaries, tri-phasic, LVOT and three user defined configurations are provided. Each configuration corresponds to the display of particular parameters. Alternatively, many other configurations can be provided in the menu structure.

Based on the selected configuration, the microprocessor 24 determines which parameters are calculated and displayed. For example, if a carotid artery configuration is selected, four parameters are calculated and displayed: maximum velocity, minimum velocity, Doppler flow angle and heart rate. The parameters associated with each of the configurations for the preferred embodiment are shown in FIGS. 5B–F as "on". Generally, acceleration, acceleration time and ejection time are not used by any of the configurations of the preferred embodiment. However, the user may select one of these parameters for a user defined configuration.

Referring now to FIG. 7, parameter calculator 52 receives the input selecting a configuration as shown by block 70. The parameters for calculation are then selected from a table, as represented by block 72. Generally, the table stores the information represented in FIGS. 5B–F. The selected parameters from block 72 are calculated, as represented by block 74. The calculations used to obtain each parameter are those known in the art and provided in the microfiche appendix in file adcompute.c.

Other than predefined configurations, such as carotid, user defined configurations are provided. User defined configurations allow the user to adjust which parameters are displayed on display 28. A menu listing various parameters is provided on display 28 as a set-up function. The list of parameters is shown in FIG. 5A. The microprocessor 24 controls interaction between user interface 60 and display 28 as known in the art. Depression of a hard key on keyboard 63 activates the menu. Using the trackball 61 to move a cursor the user selects desired parameters for calculation and display by depressing a soft key 65. The user created configuration results in a table, such as shown in FIG. 5A. The user created configuration table is stored for later use in the maximum velocity mode.

Once the user selects the parameters for display, the ultrasound system is used in the maximum velocity mode. Processing of the echo signals is started. Parameter calculator 52 then calculates the selected parameters, and microprocessor 24 causes the parameters to be displayed on display 28. Thus, parameter selection is simplified through selection of the configuration.

To further simplify user adjustment, a signal type is selected by the user. Signal types correspond to listings of input variables for maximum velocity processor 30. The signal type provides the value of $S_n$, frequency group selection, noise signal sample rate, noise threshold, maximum allowed jump, bins and the median filter length. Preferably, the signal types include high volume, low resistance, triphasic, and LVOT. Other signal types may be provided. Preferably, the variables for any other signal types are selected based on experience and the desired output.

Preferably, selection of the configuration as discussed above also selects the signal type. The microprocessor 24 selects the signal type based on the configuration selection. The microfiche appendix provides the preferred signal type input variables in file "signal type". The microprocessor 24 uses the signal type input variables to control maximum velocity processor 30.

For example, if a high volume signal type is chosen, the algorithm is applied by maximum velocity processor 30 only to positive frequency sample points 47. If a triphasic signal type is selected, the algorithm is applied to both negative and positive frequencies. Further, if a low resistance signal type is selected, the default output is selected as the baseline frequency. $S_n$ may, for example, be set equal to 4.0 for low resistance signal type.

As another example, the user may select a left ventricle outflow track (LVOT) configuration. The LVOT configuration references a LVOT signal type. Thus, only positive frequencies are examined by maximum velocity processor 30 and the default output is set to zero order hold Further, $S_n$ is selected as 3.5. For the LVOT configuration, the velocity time integral, cardiac output, heart rate, and maximum velocity parameters are calculated and displayed. Additionally, a diameter of the LVOT vessel is displayed.

The diameter is not obtained from the maximum velocity curve 50. Another input is used to determine the diameter. Referring to FIG. 7, the vessel diameter is obtained by manual caliper measurement as represented by block 80. Referring to FIG. 1 and as known in the art, the user places calipers on opposite sides of the vessel on a two-dimensional ultrasound display with user interface 60. The microprocessor 24 calculates the diameter of the manual trace as represented by block 82 in FIG. 7. Since the vessel is typically circular, the diameter is used for determining the LVOT area. Alternatively, the diameter of the LVOT vessel may be determined by a calculation package in ultrasound system 20, as known in the art.

As represented by block 84 in FIG. 7, the area from the manually measured diameter is multiplied by the heart rate and the velocity time integral parameters. The result is a measurement indicative of cardiac output.

The description above, including parameter calculations, applies to real time acquisition and display of echo signals. Many of the same methods also apply to echo signals recorded in and played back from CINE 90. The user selects playback of signals from CINE 90 in the maximum velocity mode. As known in the art a hard key on keyboard 63 is depressed to trigger playback of recorded echo signals. The microprocessor 24 controls playback from CINE 90. CINE 90 provides earlier acquired echo signals to maximum velocity processor 30. The earlier acquired echo signals are also displayed on display 28 as known in the art. The display is of a frown Doppler strip. Preferably, the Doppler strip corresponds to multiple heartbeats.

Use of the system in the CINE 90 based mode provides further user fine tuning for calculation of parameters. Parameter calculator 52 calculates any time period sensitive parameters based on the time period between two delimiters 92 and 94. The delimiter generator 62 of FIG. 1 generates the two delimiters 92, 94 (shown in FIG. 2D) on display 28. Delimiter generator 62 is part of microprocessor 24. Selection of CINE mode causes the microprocessor 24 to generate delimiters 92 and 94. Preferably, delimiter 92 is automatically displayed at the beginning of a heartbeat. Delimiter 94 is preferably displayed at the end of a heartbeat. The heart cycle algorithm discussed above determines any relevant heart cycle periods.

Parameter calculator 52 determines various parameters based on the location of delimiters 92 and 94. For example, the maximum velocity for a heartbeat is calculated between delimiters 92 and 94. Using soft keys 65, the user selects a delimiter 92 or 94, such as delimiter 92. The user moves the track ball 61 to move the delimiter along the frown Doppler strip 100. The user also selects delimiter 94 using soft keys 65. The user moves trackball 61 to move delimiter 94. Repositioning either delimiter 92–94 adjusts the time period for parameter calculation. Thus, the user adjusts the time period for parameter calculation. Only one or both delimiters may be moved.

The user selects a particular heartbeat for calculation of parameters by causing movement of delimiters 92 and 94 to the beginning and end of the heartbeat, respectively. Also by moving one or both of delimiters 92 and 94, the time period for a single heartbeat is adjusted. Thus, the user may override the microprocessor's 24 estimated start and/or end of any heartbeat.

Further, the user may position delimiters 92 and 94 to encompass several heartbeats. Parameters are then calculated over several heartbeats. Microprocessor 24 applies the data from between delimters 92 and 94 to parameter calculator 52. Microprocessor 24 calculates the parameter for each entire heart beat between delimiters 92 and 94. The values for each of the multiple heart beats are then averaged. The average value is displayed as the parameter.

The source code in the attached microfiche appendix provides one implementation of the adjustment and detection of the maximum velocity. The source code is run on microprocessor 24 and the maximum velocity processor 30.

Microfiche appendix sheets 1–5 contain code for microprocessor 24. The selection of parameters, configurations, signal types and other variable and processes discussed above are implemented with the attached source code. Generally, the code is programmed to receive inputs from user interface 60, as known in the art. The user inputs provide adjustment selection information as discussed above. The selection information includes the configuration selection, maximum velocity algorithm adjustment selection and set-up information. Set-up information comprises a selection of which of the predefined configuration are provided for maximum velocity mode selection and creation of the user defined configurations.

The code also receives time and velocity information corresponding to the maximum velocity waveform. Time is in units of pixels and velocity is in units of pixels. Statements of the inputs and functions are provided within the code. Based on the time, velocity and user input information, the microprocessor 24 uses the code to control maximum velocity processor 30 and calculate parameters as discussed above.

Microfiche appendix sheet 6 contain code for maximum velocity processor 30. The code receives bin numbers corresponding to velocity and 8 or 16 bit values corresponding to signal strength. The code also receives the variables provided from microprocessor 24. The variables are discussed above. Generally, numeric variable values are provided without units. However, the maximum allowed jump value corresponds to a certain number of bins or frequencies. The median filter length corresponds to the number of spectra filtered. As discussed above, the code outputs the maximum velocity and a time corresponding to the maximum velocity.

It should be understood that many changes and modifications can be made to the embodiments described above. For example, particular configurations and signal types have been discussed above. Other configurations and signal types are possible and may be provided for user selection. Further, Interactive Goal Directed Ultrasound Measurement System; U.S. Pat. No. 5,553,620, the disclosure of which is hereby incorporated by reference, discloses organizing an ultrasound system measurement package based upon the physiology currently being studied. It is contemplated that the organization information disclosed in that patent could be used in conjunction with the system disclosed herein. Further, input from other sources, such as manual measurements from an onboard calculation package as known in the art, may be provided to microprocessor 24 for display and parameter calculation.

It is therefore intended that the foregoing detailed description be understood as an illustration of the presently preferred embodiments of the invention, and not as a definition of the invention. It is only the following claims, including all equivalents, that are intended to define the scope of this invention.

We claim:

1. A method for interactively detecting a maximum velocity as a frequency or velocity value from acquired echo signals in an ultrasound system comprising the steps of:

operating said ultrasound system in a maximum velocity mode;

calculating a threshold as a function of at least one echo signal value, determining said maximum velocity as a function of said echo signals and said threshold, and adjusting said determining step in response to a control signal while said ultrasound system remains in said maximum velocity mode.

2. The method of claim 1 wherein the step of determining comprises determining said maximum velocity during real time processing of said echo signals.

3. The method of claim 1 wherein the step of calculating a threshold comprises the steps of:

obtaining a signal strength of one of said echo signals, said signal strength associated with a frequency selected from the group of: positive frequency farthest from a baseline frequency, negative frequency farthest from said baseline frequency and both;

multiplying said signal strength by a scale factor to determine a minimum signal threshold; and wherein the step of determining said maximum velocity comprises examining signal strengths of said echo signals, said signal strengths associated with frequencies starting from one of the group of: said positive frequency, said negative frequency, and said both, and continuing toward said baseline frequency to determine a maximum frequency, said maximum frequency associated with one of said signal strengths above the minimum signal threshold.

4. The method of claim 3 wherein the step of examining signal strengths further comprises examining said signal strengths to determine said maximum frequency based on a sequence of frequencies associated with a signal strength above the minimum signal threshold.

5. The method of claim 3 wherein the steps of obtaining a signal strength, multiplying said signal strength and examining signal strengths comprise obtaining an amplitude, multiplying said amplitude and examining amplitudes, respectively.

6. The method of claim 3 wherein the steps of obtaining a signal strength, multiplying said signal strength and examining signal strengths comprise obtaining an energy, multiplying said energy and examining energies, respectively.

7. The method of claim 1 wherein the step of adjusting comprises adjusting a scale factor.

8. The method of claim 7 wherein the step of adjusting comprises adjusting a percentage applied to said scale factor.

9. The method of claim 1 wherein the step of adjusting comprises the steps of:
displaying a percentage; and
adjusting said percentage in response to user selection.

10. The method of claim 9 further comprising displaying spectral lines.

11. The method of claim 1 wherein the step of adjusting comprises selecting a frequency group to determine said maximum velocity from one of the group of: positive frequencies, negative frequencies and both.

12. The method of claim 11 wherein said maximum velocity is determined from said both said positive and said negative frequencies, said step of determining comprising the step of determining said maximum velocity as a maximum absolute value of a first and second maxima associated with said positive and said negative frequencies, respectively.

13. The method of claim 1 wherein the step of adjusting comprises selecting a default maximum velocity output.

14. The method of claim 13 wherein the step of selecting comprises selecting one of the group of: zero-order hold, weighted mean, and baseline frequency as said default output.

15. The method of claim 14 wherein the step of selecting comprises selecting said default output in response to selection of a configuration.

16. The method of claim 1 further comprising the step of displaying said maximum velocity.

17. The method of claim 16 further comprising the step of calculating a parameter based on said maximum velocity curve.

18. The method of claim 17 wherein the step of calculating comprises calculating an actual heart rate.

19. The method of claim 18 further comprising the step of:
inputting an estimated heart rate; and
using said estimated heart rate for said calculating step.

20. The method of claim 17 wherein the step of calculating comprises calculating said parameter over a time period, the time period comprising one of: a heart beat, a portion of said heart beat and multiple heart beats.

21. The method of claim 17 further comprising the step of selecting at least said parameter in response to user selection of a configuration.

22. The method of claim 17 further comprising the step of displaying a first and second moveable delimiter; and wherein the step of processing comprises determining said maximum velocity curve during CINE playback of said echo signals.

23. The method of claim 22 wherein the step of calculating comprises calculating said parameter over a time period between said first and second delimiters.

24. The method of claim 1 wherein the step of adjusting comprises adjusting said determining step in response to selection of a signal type.

25. The method of claim 1 further comprising repeating said step of determining step over time for multiple sets of echo signals to obtain a maximum velocity curve.

26. A method for interactively detecting a maximum velocity as a frequency or velocity value from echo signals in an ultrasound system comprising the steps of:
detecting a maximum velocity as a function of a threshold determined as a function of at least one echo signal;
displaying said maximum velocity; and
altering said detecting step in real time in response to user input.

27. The method of claim 26 wherein said altering step comprises altering said detecting step in response to selection of one of the group of: a nominal scale factor, a percentage applied to a scale factor, a frequency group, a default output, a signal type and a configuration.

28. An apparatus for interactively detecting a maximum velocity as a frequency or velocity value from echo signals in an ultrasound system in a maximum velocity mode comprising:
a processor, said processor comprising maximum velocity code;
said code comprising a variable and a threshold calculated as a function of at least one echo signal value;
a user input, said user input providing a value for said variable while said ultrasound system is in a maximum velocity mode; and
at least one maximum velocity value calculated as a function of said threshold and said variable.

29. The apparatus of claim 28 wherein said variable comprises a scale factor.

30. The apparatus of claim 29 wherein said scale factor comprises a nominal scale factor.

31. The apparatus of claim 29 wherein said scale factor comprises a percentage.

32. The apparatus of claim 28 wherein said maximum velocity code comprises application of a D'Alessio algorithm.

33. The apparatus of claim 28 wherein said processor comprises a Digital Signal Processor.

34. The apparatus of claim 28 wherein said user input comprises a device selected from the group of: a trackball, a soft key and both said trackball and said soft key.

35. The method of claim 34 further comprising the step of displaying said maximum velocity curve.

36. The method of claim 34 further comprising the step of calculating a parameter as a function of the maximum velocity curve.

37. The method of claim 36 further comprising the step of selecting said parameter in response to selecting said configuration.

38. The method of claim 36 further comprising calculating at least a second parameter as a function of the maximum velocity curve.

39. The method of claim 38 further comprising the steps of:
  selecting at least one of multiple parameters for calculation in response to selection of said configuration; and
  displaying said multiple parameters.

40. The method of claim 36 wherein:
  the step of selecting comprises selecting a left ventricle outflow tract configuration; and
  the step of calculating comprises multiplying a heart rate parameter by a velocity time integral parameter by a left ventricle outflow tract area.

41. The method of claim 36 wherein the step of calculating comprises calculating said parameter over a time period, the time period comprising one of: a heart beat, a portion of said heart beat and multiple heart beats.

42. The apparatus of claim 28 further comprising a second processor, said second processor in communication with said processor and said user input.

43. The apparatus of claim 42 further comprising a display, said display operatively connected to an output of said second processor.

44. The apparatus of claim 43 wherein said display operatively connects to a spectral Doppler output and a maximum velocity output of said second processor.

45. The apparatus of claim 28 wherein said variable comprises a frequency group selected from the group of: positive frequencies, negative frequencies and both said positive and said negative frequencies.

46. A method for interactively detecting a maximum velocity from echo signals in an ultrasound system comprising the steps of:
  selecting a configuration during a maximum velocity mode;
  processing said echo signals;
  determining said maximum velocity in response to said processing; and
  adjusting said determining in response to said selection of said configuration.

47. The method of claim 46 wherein the step of selecting comprises selecting a menu item.

48. The method of claim 46 wherein the step of selecting comprises selecting said configuration prior to processing said echo signals.

49. The method of claim 46 wherein the step of determining comprises determining the maximum velocity of said echo signals during real time acquisition of said echo signals.

50. The method of claim 46 further comprising selecting a signal type in response to said selection of said configuration, and wherein said adjusting step is in response to said selecting said signal type.

51. The method of claim 46 wherein the step of determining comprises the steps of:
  obtaining a signal strength of one of said echo signals, said signal strength associated with a frequency selected from the group of positive frequency farthest from a baseline frequency, negative frequency farthest from said baseline frequency and both;
  multiplying said signal strength by a scale factor to determine a minimum signal threshold, and
  examining signal strengths of said echo signals, said signal strengths associated with frequencies starting from one of the group of said positive frequency, said negative frequency, and said both, and continuing toward said baseline frequency to determine a maximum frequency, said maximum frequency associated with one of said signal strengths above the minimum signal threshold.

52. The method of claim 51 wherein the step of examining signal strengths further comprises examining said signal strengths to determine said maximum frequency based on a sequence of frequencies associated with a signal strength above the minimum signal threshold.

53. The method of claim 51 wherein the steps of obtaining a signal strength, multiplying said signal strength and examining signal strengths comprise obtaining an amplitude, multiplying said amplitude and examining amplitudes, respectively.

54. The method of claim 46 wherein the step of adjusting comprises adjusting a scale factor.

55. The method of claim 46 wherein the step of adjusting comprises selecting a frequency group to determine said maximum velocity from one of the group of: positive frequencies, negative frequencies, and both said positive and said negative frequencies.

56. The method of claim 55 wherein said maximum velocity is determined from said both said positive and said negative frequencies, said step of processing comprising the step of determining said maximum velocity as a maximum absolute value of a first and second maxima associated with said positive and said negative frequencies, respectively.

57. The method of claim 46 wherein the step of adjusting comprises selecting a default output for when all signal strengths associated with said echo signals are examined and said signal strengths are below a minimum signal threshold, said default output selected from the group of: zero-order hold, weighted mean and baseline frequency.

58. The method of claim 46 wherein the step of selecting comprises selecting a left ventricle outflow tract configuration.

59. The method of claim 46 wherein the step of selecting comprises selecting a signal type.

60. The method of claim 46 further comprising the step of displaying said maximum velocity.

61. The method of claim 46 further comprising repeating said step of processing for multiple sets of echo signals to obtain a maximum velocity curve.

62. An apparatus for interactively detecting a maximum velocity from echo signals in an ultrasound system comprising:
  a processor, said processor comprising configuration code and maximum velocity code;
  said configuration code comprising multiple configuration data;
  said maximum velocity code comprising a variable;
  a user input, said user input providing data to select at least one of said multiple configuration data during processing of the maximum velocity code; and
  said at least one configuration data providing a value for said variable.

63. The apparatus of claim 62 wherein said multiple configurations comprise at least a left ventricle outflow tract configuration.

64. The apparatus of claim 62 where said processor comprises:
  a first processor, said first processor comprising said maximum velocity code;
  a second processor, said second processor comprising said configuration code.

65. The apparatus of claim 64 wherein said first processor is a digital signal processor.

66. The apparatus of claim 62 wherein said variable comprises a scale factor.

67. The apparatus of claim 66 wherein said scale factor comprises a nominal scale factor.

68. The apparatus of claim 62 wherein said maximum velocity code comprises code derived from a D'Alessio algorithm.

69. The apparatus of claim 62 wherein said user input comprises one of the group of: a trackball, a soft key and both said trackball and said soft key.

70. The apparatus of claim 62 further comprising a display, said display operatively connected to an output of said processor.

71. The apparatus of claim 70 wherein said output provides spectral Doppler output data.

72. The apparatus of claim 71 wherein said display is operatively connected to said processor for receiving said maximum velocity.

73. The apparatus of claim 70 wherein said output provides menu screen data.

74. The apparatus of claim 73 wherein said display has a menu display.

75. The apparatus of claim 62 wherein said variable is a selection of frequencies from group of: positive frequencies, negative frequencies and both said positive and said negative frequencies.

76. A method for providing a measurement of cardiac output based on echo signals in an ultrasound system comprising the steps of:

processing said echo signals to determine a maximum velocity;

inputting a diameter of a left ventricle outflow tract manually;

determining velocity time integral from said maximum velocity and a heart rate; and multiplying said heart rate by said velocity time integral by an area derived from said diameter to obtain a measurement indicative of the cardiac output.

77. The method of claim 76 further comprising the step of displaying said cardiac output as a quantity.

78. The method of claim 76 further comprising the step of selecting a left ventricle outflow tract configuration of said ultrasound system, said multiplying step performed in response to selection of said left ventricle outflow flow tract configuration.

79. The method of claim 76 further comprising the step adjusting said processing.

80. The method of claim 79 wherein the step of adjusting said processing further comprises adjusting said processing in response to selection of said left ventricle outflow tract configuration.

81. The method of claim 76 further comprising the step of repeating said processing and multiplying steps for multiple sets of said echo signals.

82. An apparatus for providing cardiac output from echo signals in an ultrasound system comprising:

a processor, said processor comprising maximum velocity code for determining a maximum velocity;

determining with said processor, a heart rate and a velocity time integral from said maximum velocity;

a user input operatively connected to said processor, said user input providing a diameter input data;

a multiplier, said multiplier for multiplying said diameter input data with said heart rate and said velocity time integral to obtain a measurement indicative of cardiac flow.

83. The apparatus of claim 82 wherein said processor comprises:

a first processor comprising said maximum velocity code; and a second processor operatively connected to said first processor and said user input for performing said determining step.

84. The apparatus of claim 83 wherein said first processor comprises a digital signal processor.

85. The apparatus claim 82 wherein said maximum velocity code comprises a variable and said user input provides variable selection data.

86. The apparatus of claim 85 wherein said user input provides a configuration selection data and said configuration data provides a value for said variable.

* * * * *

UNITED STATES PATENT AND TRADEMARK OFFICE
CERTIFICATE OF CORRECTION

PATENT NO. : 5,868,676
DATED : February 9, 1999
INVENTOR(S) : Laurence S. McCabe et al.

It is certified that error appears in the above-indentified patent and that said Letters Patent is hereby corrected as shown below:

On the Title Page

In column 1, item [75], line 2, change "Moutain View" to --Mountain View--.

In column 2, line 13, under "OTHER PUBLICATIONS" change "normalised" to --normalized--.

In page 2, column 1, line 23, under "OTHER PUBLICATIONS" change "analysed" to --analyzed--.

In page 2, column 2, line 10, change "$\sqrt{71}$" to --$\sqrt{f}$--.

In page 2, column 2, line 16, change "'Objective$^\alpha$" to --'Objective'--.

In column 5, line 39, change "non noise" to --non-noise--.

In column 6, line 33, change "limiations" to --limitations--.

In column 7, line 43, change "," (comma) to --.-- (period).

UNITED STATES PATENT AND TRADEMARK OFFICE
CERTIFICATE OF CORRECTION

PATENT NO. :     5,868,676
DATED       :    February 9, 1999
INVENTOR(S) :    Laurence S. McCabe et al.      Page 2 of 2

It is certified that error appears in the above-identified patent and that said Letters Patent is hereby corrected as shown below:

In column 12, line 43, after "hold" insert --.-- (period).

In column 13, line 9, change "frown" to --frozen--.

In column 13, line 29, change "frown" to --frozen--.

In column 13, line 46, change "delimters" to --delimiters--.

In column 13, line 48, change "deliniters" to --delimiters--.

In column 13, line 65, change "predefined" to --pre-defined--.

Signed and Sealed this

Thirtieth Day of May, 2000

Attest:

Q. TODD DICKINSON

Attesting Officer          Director of Patents and Trademarks